United States Patent [19]

Traina et al.

[11] Patent Number: 5,458,010
[45] Date of Patent: Oct. 17, 1995

[54] VACUUM DILUTION EXTRACTION GAS SAMPLING SYSTEM

[75] Inventors: John E. Traina, Glenshaw; Richard Myers, Gibsonia, both of Pa.

[73] Assignee: United Sciences, Inc., Gibsonia, Pa.

[21] Appl. No.: 218,563

[22] Filed: Mar. 28, 1994

Related U.S. Application Data

[63] Continuation-in-part of Ser. No. 789,935, Nov. 12, 1991, Pat. No. 5,297,432.

[51] Int. Cl.$^6$ ...................................................... B01L 7/00
[52] U.S. Cl. .................... 73/864.12; 73/864.34; 73/117.3
[58] Field of Search ................................. 73/116, 117.3, 73/864.34, 864.35, 864.83, 864.12

[56] References Cited

U.S. PATENT DOCUMENTS

| | | | |
|---|---|---|---|
| 3,817,100 | 6/1974 | Anderson | 73/213 |
| 4,596,156 | 6/1986 | Shimizi | 73/863.31 |
| 4,686,847 | 8/1987 | Aramaki | 73/23 |
| 4,823,591 | 4/1989 | Lewis | 73/3 |
| 4,974,455 | 12/1990 | McGowan et al. | 73/863.12 |
| 5,138,163 | 8/1992 | Buller et al. | 73/116 |

FOREIGN PATENT DOCUMENTS

0503996A1  9/1992  European Pat. Off. .

OTHER PUBLICATIONS

Richard L. Myers and Donald Vernon, "Field Experiences Using Dilution Gas Probe Techniques for Continuous Source Emission Monitoring," *Proceedings of the Controls West Conference*, pp. 347–355, submitted to the International Industrial Controls Conference and Exhibition/Controls West '85, Long Beach Convention Center, Long Beach, Calif., Sep. 16–18, 1985.

"Model 797: Diluting Stack Sampler," *EPM Environmental Product Brochure*.

"Chapter 6: Extractive System Design," *EPA Handbook: Continuous Air Pollution Source Monitoring* Systems, pp. 6–1 to 6–18 (Jun. 1979).

"Inertial Dilution System: AR-120", Anarad Inc., Santa Barbara, Calif.

Patent Abstrafts of Japan, vol. 009, No. 320, (P-413) 14 Dec., 1985 & JP-A-60 147 635 (Toyota Jidosha KK) 3 Aug. 1985.

Patent Abstracts of Japan, vol. 011, No. 354, (P-638) 19 Nov., 1987 & JP-A-62 133 336 (Nippon Soken, Inc., Others: 01) 16 Jun., 1987.

*Primary Examiner*—Richard E. Chilcot, Jr.
*Assistant Examiner*—Max H. Noori
*Attorney, Agent, or Firm*—Buchanan Ingersoll; Lynn J. Alstadt

[57] ABSTRACT

A gas sampling system utilizing a pair of parallel sonic orifices. One of the orifices is connected to a source of filtered, heated samples. The second, larger orifice is connected to a source of dilution gas. A vacuum pump maintains a substantial vacuum behind the orifices, thus assuring critical flow therethrough. The sample and diffusion gas are mixed behind the orifices and transported under partial vacuum for analysis. The dew point of the sample is affected by both the ratio of the diameter of orifices and the degree of vacuum transporting the gas mixture. As such, the dew point can be varied indefinitely by any reasonable combination of orifice ratio and vacuum pump strength.

11 Claims, 8 Drawing Sheets

5,458,010

VACUUM DILUTION EXTRACTION GAS SAMPLING SYSTEM

RELATED APPLICATION

This application is a continuation-in-part of U.S. patent application Ser. No. 07/789,935, filed Nov. 12, 1991 now U.S. Pat. No. 5,297,432.

BACKGROUND OF THE INVENTION

1. Field of the Invention

This invention generally relates to extractive gas sampling systems such as are used for analysis of process gases or fossil fuel combustive gases being vented through a stack.

2. Description of the Prior Art

An important category of extractive gas sampling relates to the compliance monitoring requirements enforced by the United States Environmental Protection Agency (EPA). Many sources of air pollution, such as fossil-fueled power plants, incinerators, metal smelters, and cement kilns, are required to monitor levels of certain gaseous species that are released into the atmosphere. These species include sulfur dioxide, nitrogen oxides, carbon monoxide, carbon dioxide and oxygen. The EPA standards for compliance monitoring systems are delineated in Volume 40 of the Code of Federal Regulations.

The gas streams to be monitored typically have certain intrinsic characteristics which complicate testing. For example, they generally contain 6% to 20% by volume of evaporated moisture, which results in a sample dew point well above that of normal ambient temperatures. Also, the gas streams often contain significant amounts of condensed moisture in the form of entrained water droplets and fog. Acid gases, such as sulfur dioxide are also generally present. Additionally, the gas streams invariably contain large quantities of particulate debris such as soot, fly-ash from fossil fuels and process material.

In order to analyze a sample for its gaseous constituents, it is necessary to remove the particulates and transport the sample to a remote location suitable for the operation of gas analysis instrumentation. For accurate measurements and for reliability of the test equipment, it is necessary to ensure that moisture and gases will not condense either in the sample probe, the sample lines, or the analyzers. However, the methods used to accomplish these goals must not themselves alter the samples in a way that negatively impacts nesting accuracy. In the past, two basic types of sampling systems have been developed for analysis of gaseous mixtures.

The first type, the traditional extractive system, is shown in FIG. 1. Many vendors have supplied similar systems over the years. This system, however, has proved to have many undesirable drawbacks as described below.

The second type, illustrated in FIG. 2, is a venturi dilution probe system. This type of system was developed in the 1980s primarily in response to perceived inadequacies with the traditional system. As discussed more fully below, however, the venturi probe system is also not without disadvantages.

SUMMARY OF THE INVENTION

A gas sampling system practicing the present invention utilizes a pair of sonic orifices. One of the orifices is connected to a source of filtered, heated samples. The second, larger orifice is connected to a source of dilution gas. A vacuum pump maintains a substantial vacuum behind the orifices, thus assuring critical flow therethrough. The sample and diffusion gas are mixed behind the orifices and transported under partial vacuum for analysis. The dew point of the sample is affected by both the ratio of the diameter of orifices and the degree of vacuum transporting the gas mixture. As such, the dew point can be varied practically indefinitely through an optimum combination of orifice ratio and vacuum pump strength.

DETAILED DESCRIPTION

Prior Art Systems

Figure 1:
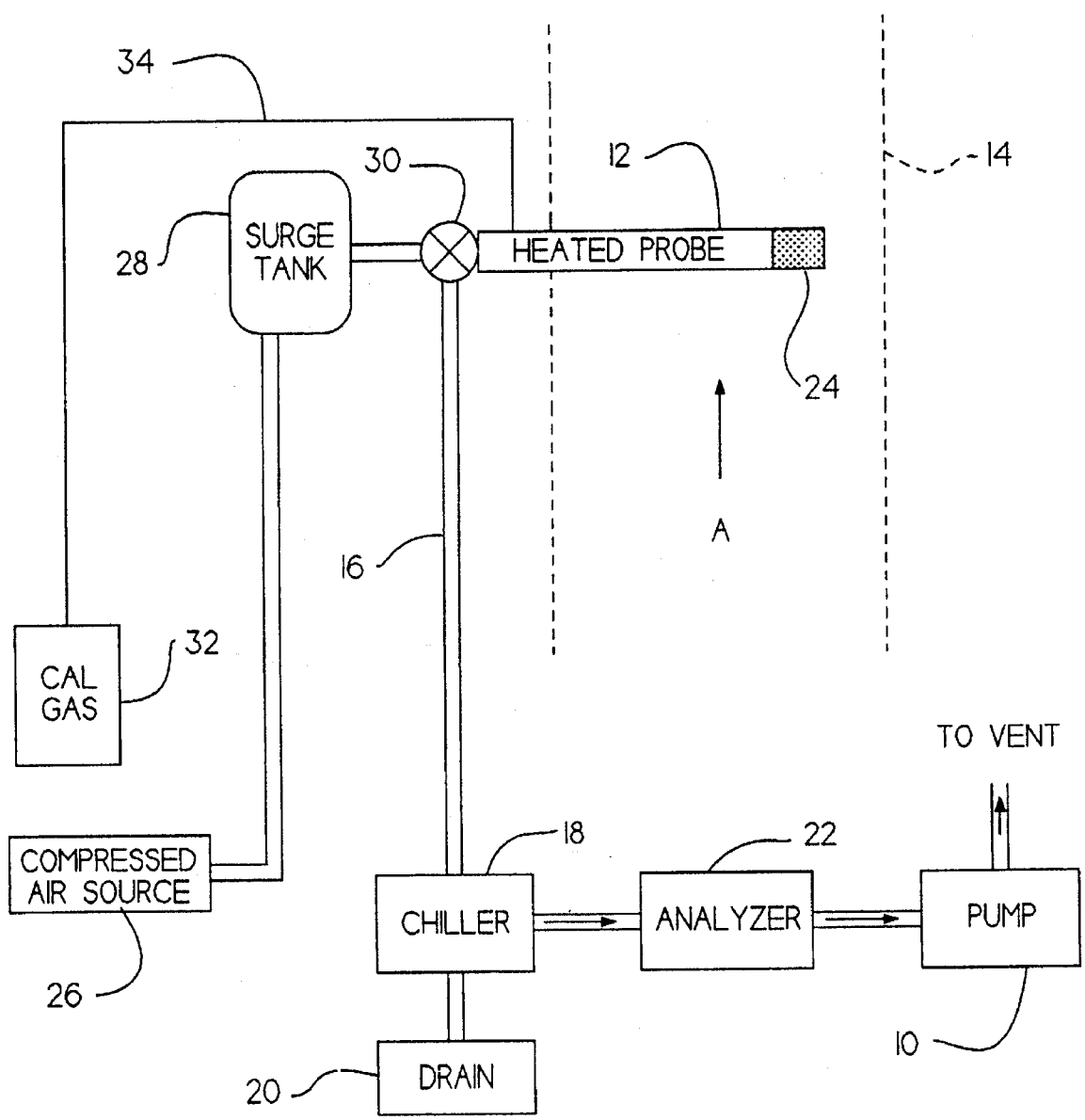
FIG. 1 is a diagram of a prior art system utilizing a heated sample line for transporting the sample.

FIG. 1 illustrates the traditional extractive system. Pump 10 draws gas through heated probe 12 from a gas stream moving within stack 14 as shown by arrow A. The sample is then transported to a remote location through a heat-traced sample line 16. Typically, probe 12 and sample line 16 are heated to about 250° F. to prevent condensation of the moisture or acid in the sample. Next, the sample is drawn through a "chiller" 18 which lowers the sample temperature to approximately 35° F. The water vapor thus condenses and is drained away at drain 20. The sample, now dry, is then reheated and transported through analyzer 22 which measures the constituents of interest. The gas sample is maintained at or near atmospheric pressure during all of this process.

A number of minor variations have been made on this basic design. Sometimes the pump is located before the analyzer. Sometimes the gas sample is diluted via the addition of nitrogen or air prior to analysis for the purpose of bringing the sample concentration within the range of the analyzers or for the purpose of reducing certain interferences within the analyzers. The analyzer and sample pump are sometimes heated so that the chiller may be omitted.

This traditional design presents a number of drawbacks and limitations. First, in order to move the sample to a remote location within an acceptable time period (EPA requires a 15 minute system response time, and process applications demand even a quicker response) the sample must be large—typically in the order of two to five liters per minute. Because the amount of particulate associated with such large samples would quickly clog any fine filter, only a coarse filter 24, such as the type constructed of sintered metal or ceramic, can be used. Even a coarse filter, however, will tend to clog every few hours in this system. To clean the filter, a blow-back design is required. For this purpose, compressed air source 26 feeds surge tank 28 which is located near ball valve 30. When valve 30 opens pressurized air in tank 28 is released, thereby purging filter 24 of impurities. Since valve 30 is continually exposed to the stack sample, however, it can develop leaks which distort the sample.

This design also requires use of large amounts of calibration ("cal") gas. Cal gas is a gas sample containing a known concentration of the species to be measured. This is used to run a calibration check on the accuracy of the measuring equipment. The EPA requires that such a calibration check be run daily using "Protocol-1" gases that may typically cost $400 for a small bottle. A similar technique using "zero gas" is sometimes employed to null the species detectors. Referring again to FIG. 1, the cal gas is fed in the traditional design from cal gas source 32 through line 34 to a location on probe 12 which is behind filter 24. Thus, deleterious effects of filter 24 such as scrubbing of sulfur dioxide by alkali particles thereon are not checked by the cal gas. In addition, a large volumetric flow of cal gas greater than the volumetric flow through tube 16 is required.

The design has a number of "weak links", which make it inherently unreliable. For example, if chiller 18 fails, analyzer 22 and pump 10 will likely be destroyed. Additionally, failure of heat tracing sample line 16 will result in condensation and contamination that can necessitate replacement of the line and all downstream plumbing. Heat traced line is significantly more expensive than unheated line. Also, since ball valve 30, analyzer 22 and pump 10 are exposed to high levels of acidic gases and to the fine particulates which permeate coarse filter 24, the service life of these components is reduced considerably.

Furthermore, when this design utilizes a chiller, a serious measurement methodology problem is presented. Specifically, gas concentrations are measured on a dry basis (i.e. with the moisture removed). Pending EPA regulations strongly favor making the concentration measurement on a wet basis (including vapor-phase moisture).

Figure 2:
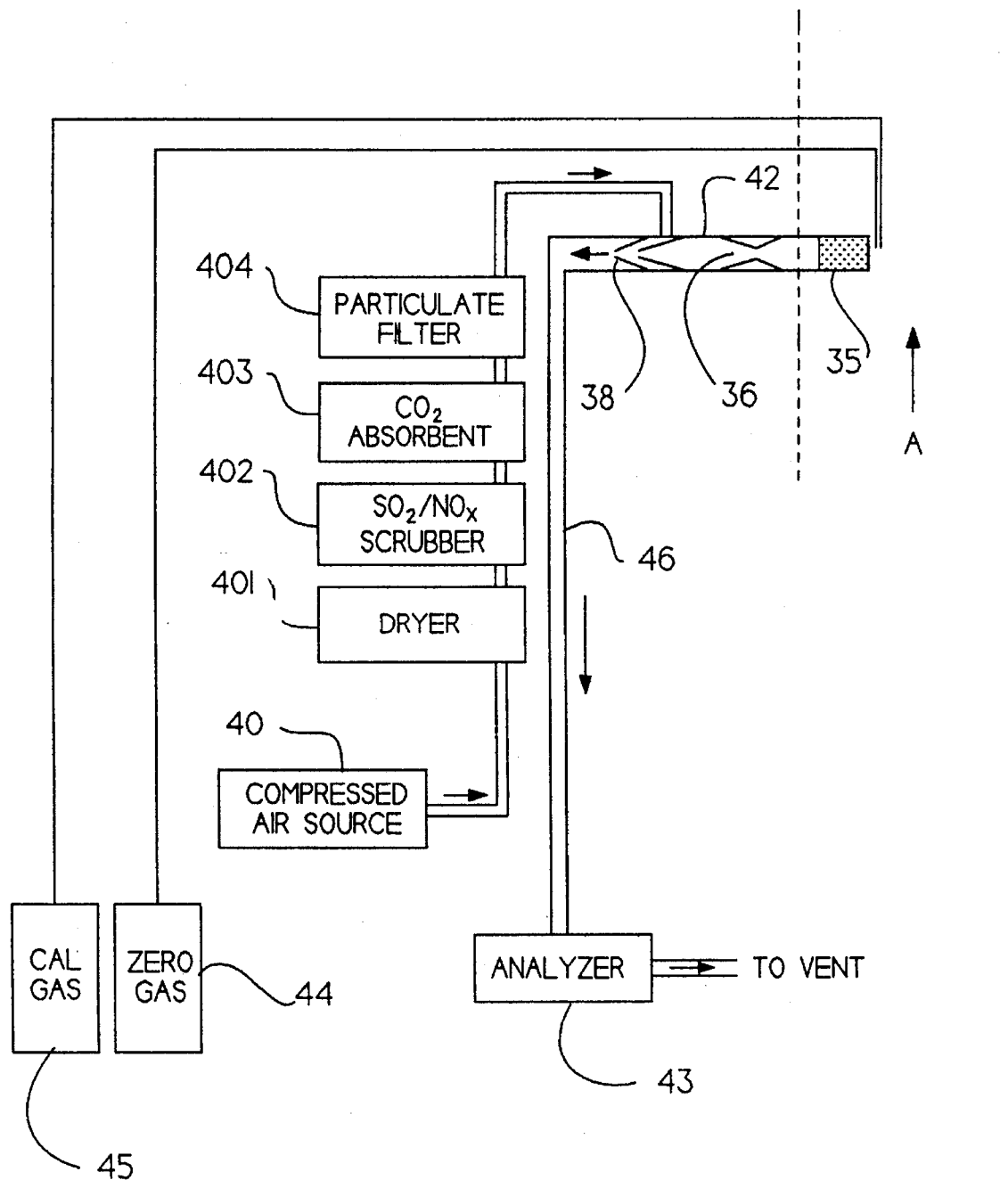
FIG. 2 is a diagram of a prior art system utilizing a dilution probe.

The second general type of prior art system, the dilution probe, is depicted as FIG. 2. In this design, the rate of stack sample extraction is considerably smaller than is the case with the traditional system of FIG. 1. Here, gas is drawn through a fine filter 35 into a device known as a "sonic orifice" or "critical-flow orifice." Sonic orifice 36 is so called because it meters a constant volumetric flow provided that a substantial vacuum exists behind the orifice. Stated another way, a pressure drop of greater than two to one (2:1) thereacross will induce a generally constant volumetric flow as metered from the upstream side of the orifice. Orifice 36 can typically be sized to permit flow as low as 20 cc per minute and as much as 200 cc per minute. Vacuum on the back side of orifice 36 is maintained by a venturi 38 which is driven by compressed air source 40. Venturi 38 also serves to provide clean, dry dilution air which lowers the sample point. The entire venturi/orifice assembly is constructed within nonheated probe 42 such that the dilution is accomplished at essentially stack temperature. The diluted sample is then sent to analyzer 43 at approximately atmospheric pressure.

This technique overcomes some of the deficiencies of the traditional extraction system. For example, cal gas 44 and zero gas 45 may be introduced upstream of filter 35 which will allow checking of deleterious filter effects. However, significant drawbacks remain. For example, because orifice 36 is a true critical-flow device, while venturi 38 is not, the dilution ratio is a function of temperature. If the process temperature varies considerably, the probe will need to be temperature controlled. Additionally, if the gas stream being sampled is fully saturated, condensation will occur on filter 35 and orifice 36 before dilution can occur. In addition, condensation will occur just downstream of the orifice 36 due to adaibetic cooling of gas passing through. In these applications, it therefore is necessary to heat the probe anyway.

Furthermore, in order to prevent condensation in unheated transport line 46, it is necessary to lower the dew point to below the expected ambient temperature. In cold climates, dilution ratios of up to 350:1 are needed. Ratios of this magnitude pose several problems. First, the concentration of the gas constituents of interest may be lowered to a level below the sensitivity of commercially available analyzers. For example, the best carbon monoxide analyzers can only measure down to five parts-per-million (5 ppm) with good accuracy. Many facilities must measure actual stack concentrations of the order of 50 ppm. Stack gas having about 50 ppm of a constituent diluted by the dilution ratio achieved in the prior art system of FIG. 2 reduces the concentration to well below 5 ppm. Another problem with high dilution ratios is that the overall system will become sensitive to minute impurities in the dilution air. As an illustration, 0.1 ppm of CO in the dilution air of the above example will be measured by the system as $(350) \times (0.1 \text{ ppm})$, the product of which is thirty-five parts per million (35 ppm). The analyzer will be unable to differentiate between this error and a comparable stack level of CO.

Moreover, the only commercially available version of this device uses a venturi that is operational only with flows of between four and seven liters per minute. This also poses several problems. For example, this large a flow of the dilution gas effectively militates against the use of bottled gas which would be prohibitively expensive and require frequent maintenance. Thus, compressed air source 40 is a compressor which utilizes the air in or near the stack. That air contains particulates, $CO_2$, $SO_x$, $NO_x$ and water vapor. Consequently, one must use an array of dryers 401, scrubbers 402, absorbants 403 and filters 404 to remove contaminants from the dilution gas. Since most analyzers only require a flow in the order of 0.5 liters/minute, most of the 4–7 liters of diluted sample are wasted. Another problem is that, for a given sized orifice, there are limits to the dilution ratios that can be achieved.

Additionally, venturi 38 is generally embedded in a very expensive probe assembly. Thus, contamination, such as could occur if the orifice assembly, which is typically made of glass, would break, necessitates replacement of a very expensive piece.

Gas sampling systems have also been used to evaluate exhaust emissions from internal combustion engines. Examples of such systems are disclosed in U.S. Pat. Nos. 3,817,100 to Anderson et al.; 3,965,749 to Hadden et al.; 4,823,591 to Lewis, and 5,184,501 to Lewis et al. None of these devices are suitable for delivering a diluted sample over long distances. They also use valve and orifice combinations which do not provide constant dilution ratios.

DESCRIPTION OF PRESENT PREFERRED EMBODIMENTS

In accordance with the present invention, a gas sampling extraction system is provided which overcome many of the disadvantages of the existing technology. The system utilizes a pair of sonic orifices. One of the orifices provides a constant flow of sample gas and the other provides a constant flow of dilution gas. The resulting mixture is transported under substantial vacuum and repressurized to typically about one atmosphere prior to analysis.

Figure 3:
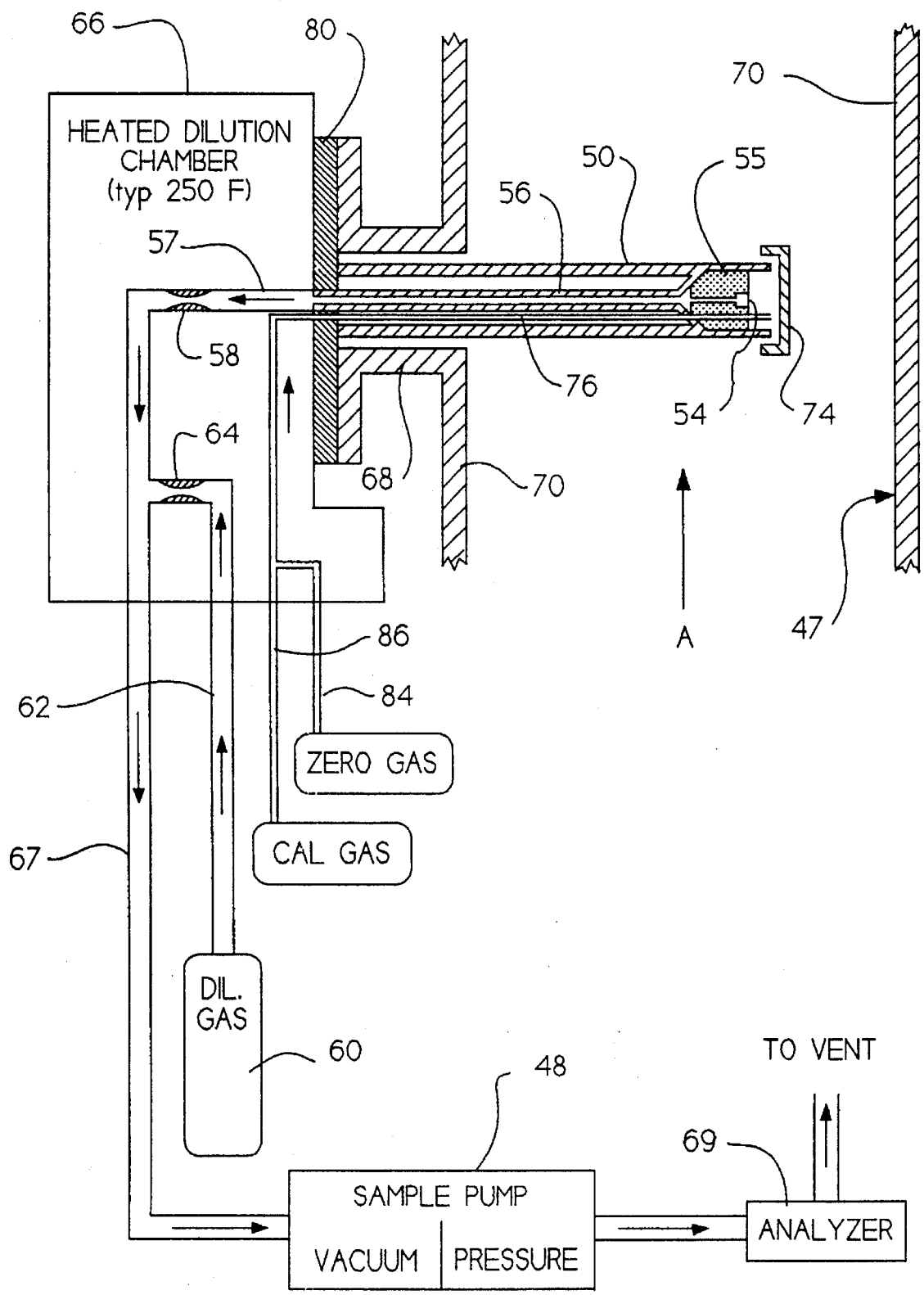
FIG. 3 is a diagram of a present preferred embodiment of the vacuum dilution extractive gas sampling system of the invention.

FIG. 3 illustrates a present preferred embodiment of the gas sampling extraction system of the invention. Gas from a system such as a gas stream moving within stack 47 is drawn by sample pump 48 into collection probe 50. The gas is preferably first filtered. Next, the sample passes through capillary tube 56 which is within probe 50. After leaving tube 56, the sample gas enters sample conduit 57 which has sample orifice 58 therein. Dilution gas is preferably simultaneously drawn at a controlled pressure by pump 48 from dilution gas source 60 into dilution gas conduit 62 and through dilution orifice 64 therein. Typical suitable dilution gases may be compressed air, carbon dioxide and nitrogen, depending on the sample gas and the analyzers which are desirable to be used. In order for the sample and dilution gas to be drawn simultaneously, orifices 58 and 64 are arranged in parallel. Specifically, conduits 57 and 62 intersect downstream of the orifices, forming mixing conduit 67 where mixing of the sample and dilution gas occurs. Since, pump 48 maintains a substantial vacuum in conduit 67, the flow rate through orifices 57 and 62 is essentially constant. Thus, a constant dilution ratio is achieved.

Conduits 57, 62 and 67 may be constructed of any suitable inert material. Some possible materials for this purpose are glass or a corrosion resistant metal alloy such as Hastalloy® corrosion resistant alloys or corrosion resistant polymeric materials such as Teflon® material. Particularly, Hastalloy® C-22 may be suitable. Orifice 58 may be as small as 0.0009 inches which corresponds to a flow rate of 4.2 cc per minute. This is much less than the minimum 20 cc per minute used in the venturi dilution system shown in FIG. 2. For a dilution ratio of 25:1, dilution orifice 64 must be five times larger in diameter than orifice 58, or 0.0045 inches in this example. This gives a flow rate of 105 cc per minute of dilution gas if the dilution gas is delivered at beneficial pressure. If the dilution gas is provided at a higher pressure, e.g., 14.7 psig, the flow will be 211 cc per minute and the dilution ratio will be 50:1. As this is a much smaller rate than the prior art, it is possible to use bottled dilution gas from gas cylinders instead of plant instrument air or compressor air. This completely eliminates problems with contamination in the dilution gas. Furthermore, by suitable selection of the orifices, it is possible to achieve any desired volumetric dilution ratio over a range of 1:1 to 250:1. For any specific set of orifices, it is possible to adjust the volumetric dilution ratio by a factor of 10, that is, over a 1:1 to 10:1 range, by simply adjusting the dilution gas pressure. Thus, the system enjoys a level of flexibility previously unattainable.

It is desirable to maintain orifices 58 and 64 in a temperature stabilized dilution chamber such as heated chamber 66. Chamber 66 is mounted engaging mounting nipple 68 which protrudes from wall 70 of stack 47. If the temperature in the dilution chamber is maintained at a fairly constant figure, the dilution ratio will be impervious to stack temperature variation. A temperature of 250° F. has been found suitable for this purpose since it is well above the dew point of most stack gases.

Typically, the dilution ratio should be chosen such that the dew point is lowered to below 30° F. Dew points below this temperature are generally not harmful to the analyzing equipment since such equipment operates at a higher temperature. Thus, condensation within the analyzer range will not occur. Generally, dilution ratios between 10:1 and 50:1 will accomplish this dew point lowering. However, a dilution ratio of even 50:1 will generally not alone lower the sample dew point enough for use in a cold climate since conduit 67 may frequently be exposed to temperatures below 30° F. For this reason, sample pump 48 transports the mixture under a substantial vacuum (0.15 atmospheric pressure) which further lowers the dew point of vapor by the factor (1/0.15)=6.67. The combination of actual volumetric dilution in vacuum transport makes it possible to lower the dew point below the coldest expected ambient temperature without actually reducing the relative concentration of the species of interest to the undesirably low levels of the prior art devices. Specifically, it is generally possible to easily lower the dew point to −25° F. using this technique.

The sample mixture next enters the vacuum side of sample pump 48 and exits the pressure side of sample pump 48 at essentially atmospheric pressure. It is not essential, however, that the analyzer 69 be placed on the pressure side of pump 48 and in other applications it may be desirable to place the analyzing equipment on the vacuum side of the pump. Thus, the species of interest are presented to analyzer 69 at a dilution ratio of only approximately 50:1 in the present example. To get the same dew point lowering with the prior art devices, the sample would have been presented to the analyzer with a dilution ratio of approximately 50:1× 6.67=333. This would be an unacceptably high dilution ratio in many cases for the reasons discussed above. Another advantage of transporting the sample under substantial vacuum is that rapid movement of the sample may be accomplished with a smaller sample rate. That is to say at reduced pressure, a sample of approximately 211 cc per minute will move through the sample line as fast as a much larger sample (211×6.67) cc/min would have moved at barometric pressure.

The preferred transport pressure for the system shown in FIG. 3 is 0.15 atmosphere or lower. Commercially available sample pumps could operate at as low as 0.075 atm. The use of more expensive sample pumps capable of achieving these lower pressures, however, is only necessary in the event that: (1) the actual dilution ratio must be kept low out of a need to operate on the range of a specific analyzer; and (2) a low ambient temperature is expected. In a warm climate it will be possible to achieve a sufficiently low dew point in conduit 67 with both a low dilution ratio and a relatively inexpensive pump. For purposes of achieving critical flow the pump only needs to achieve a vacuum of approximately 0.4 atm pressure.

Figure 4:
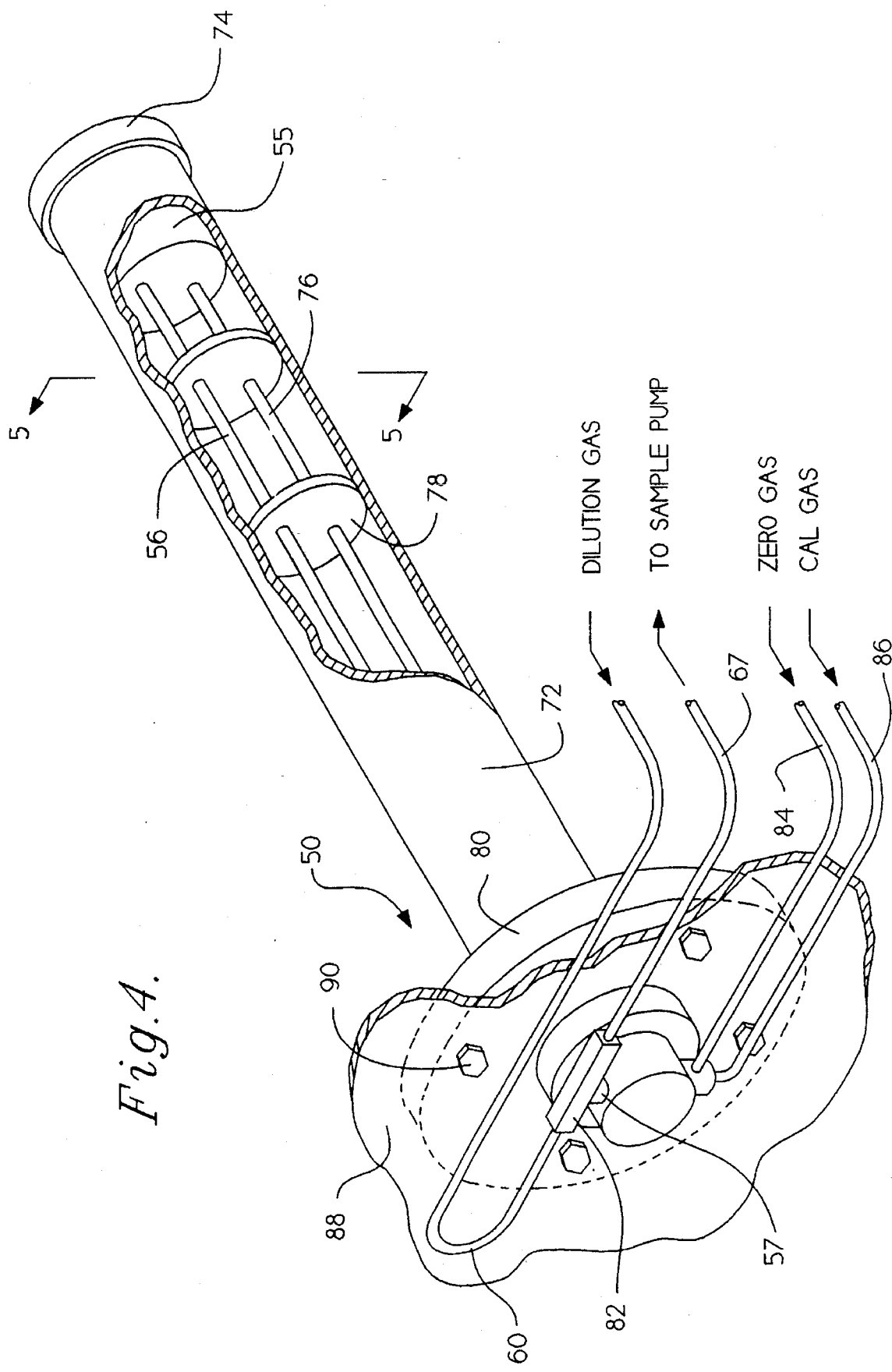
FIG. 4 is a perspective view, partially cut away of a present preferred probe for use with the invention.
Figure 5:
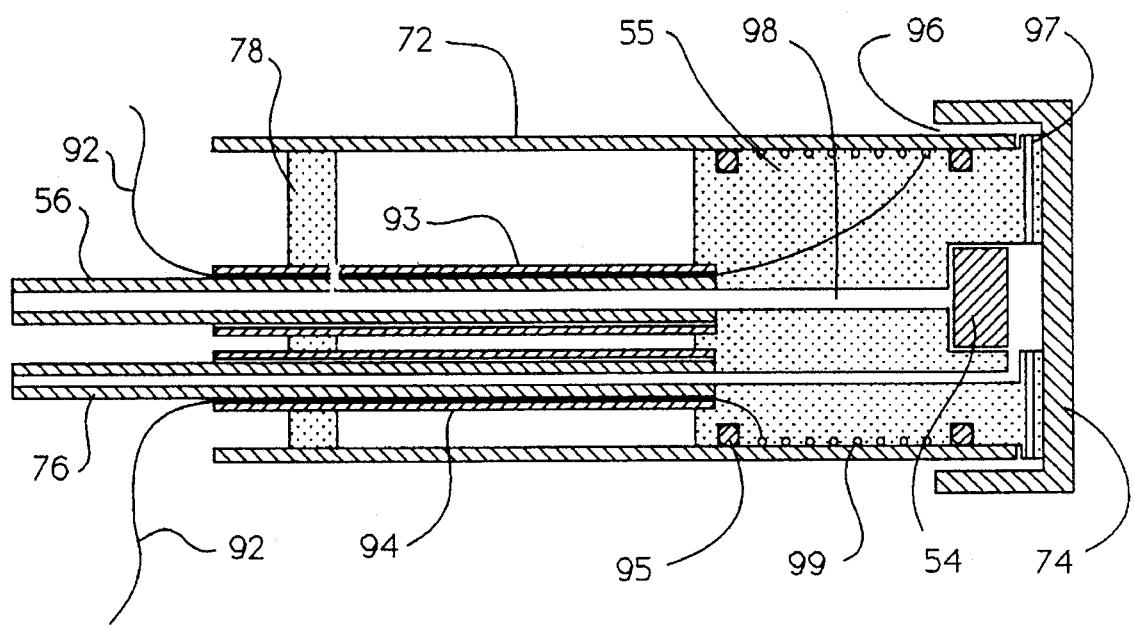
FIG. 5 is a cross-sectional view taken on a plane extending from line 5—5 to the end of the probe shown in FIG. 4.
Figure 6:
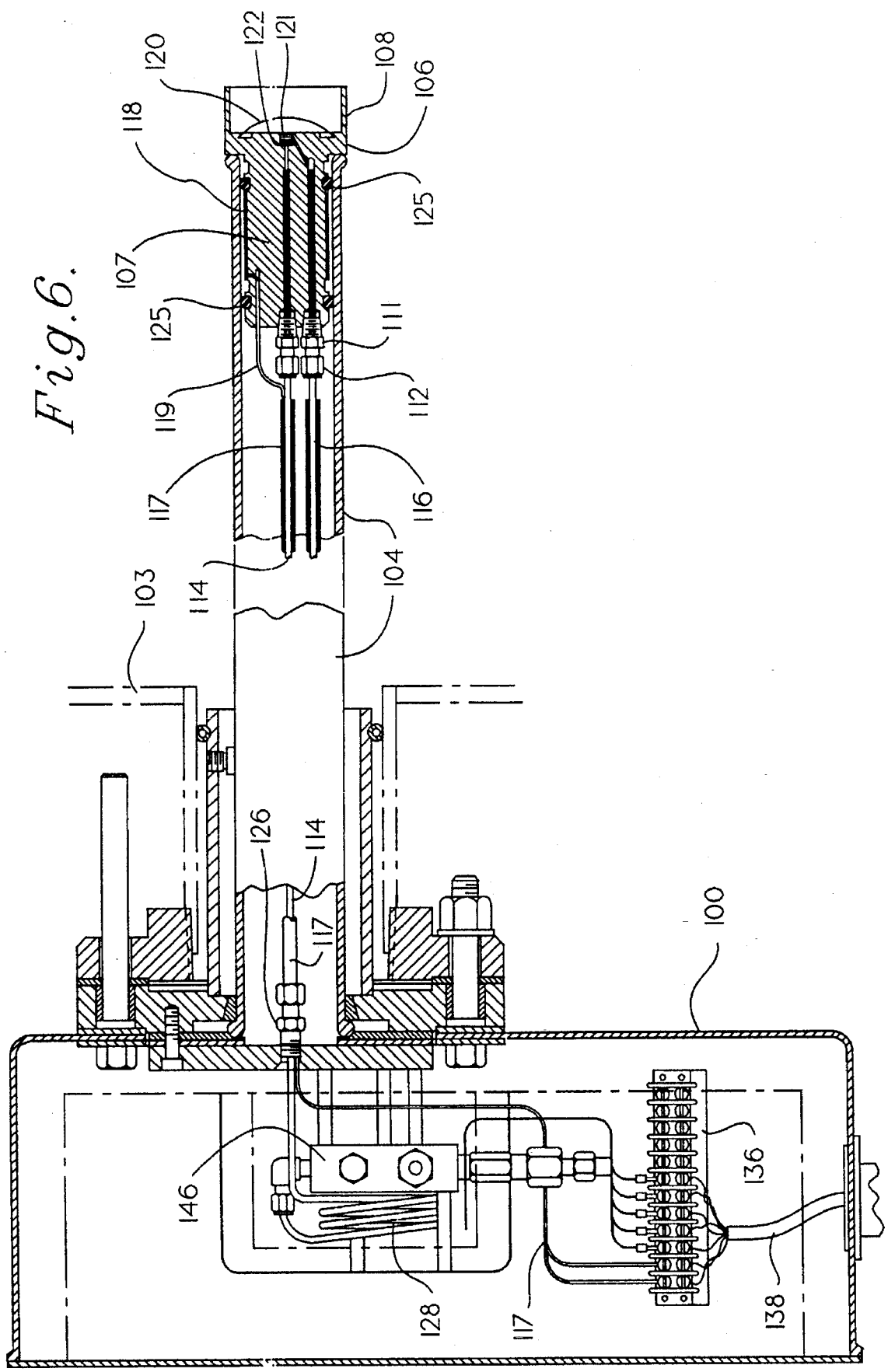
FIG. 6 is a side view partially in section of a second preferred embodiment of the vacuum dilution extractive gas sampling system.
Figure 7:
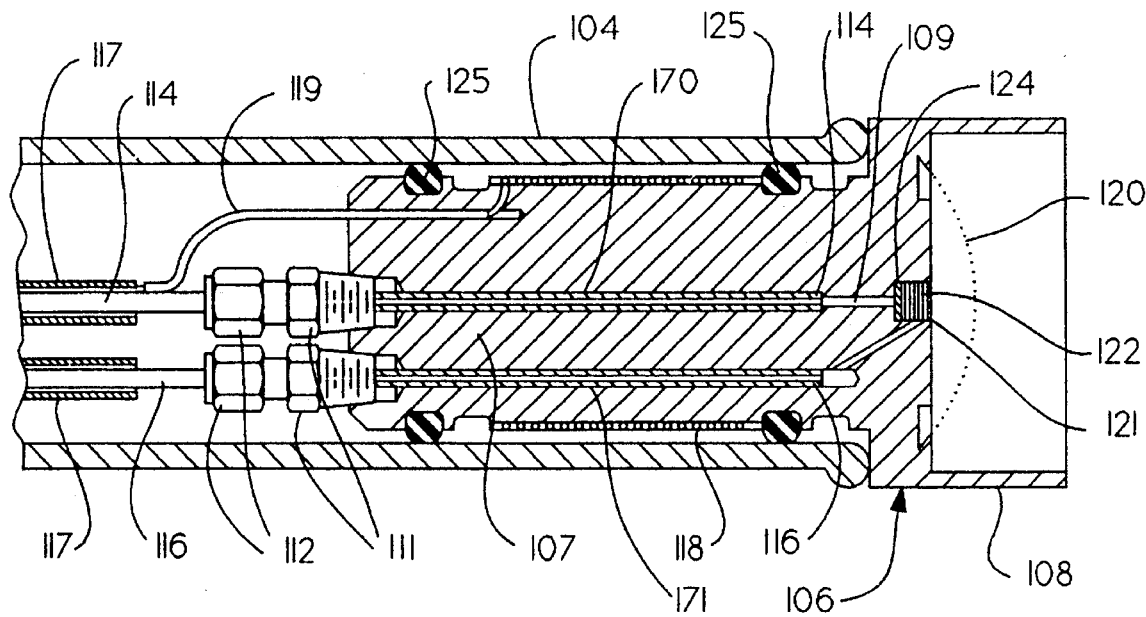
FIG. 7 is a cross-sectional view of the probe end of the embodiment of FIG. 6.

FIGS. 4 and 5 illustrate a presently preferred embodiment of a collection probe 50 practicing the present invention. Probe 50 comprises a generally hollow cylindrical body 72 which may typically be from three to six feet in length. An end cap 74 is mounted on the end of body 72 which will be exposed to the gas stream. Inside of body 72 are sample gas capillary tube 56 and cal gas capillary tube 76. Typically, these tubes would be constructed of glass, Teflon polymer or other inert material. Tube 56 and 76 both extend into filter holder which contains fine filter 54. Tube 56 terminates just downstream of filter 54 while tube 76 extends through filter holder 55 to a point just upstream of filter 54. If tubes 56 and 76 are made of glass or other fragile material, they are maintained in position within body 72 by a series of spacers, such as spacer 78. These spacers are typically constructed of a resilient material, such as Teflon® material, in order to damp vibrations and the like which could damage the tubes.

A mounting flange 80 is attached to the other end of body 72. Mounting flange 80 is adapted to engage a mounting nipple, such as nipple 68 of FIG. 3, to maintain probe 50 in position. Also at this end of probe 50 are the various plumbing connections between sample probe 50 and the rest of the system. Sample conduit 57 is shown coupled to dilution gas conduit 60 using a T-coupling 82. The mixture then exits through mixing conduit 67 to pump 48 and eventually to at least one analyzer 69. After leaving analyzer 69, the sample is generally vented to the atmosphere. Zero gas and cal gas enter tube 76 through zero gas conduit 84 and cal gas conduit 86. As discussed above, all of these connections are housed within a temperature controlled chamber 66 (FIG. 3) to maintain approximately constant flow rates. An inner wall 88 of chamber 66 is shown in FIG. 4. Wall 88 is attached to mounting flange 80 using bolts such as bolt 90.

The interior construction of the distal end of the probe is illustrated in FIG. 5. Cap 74, which is typically made of Teflon® material, contains a number of leakage paths 96 through which, for example, furnace flue gas in a stack is introduced to sample channels 97. Channels 97 are situated within filter holder 55 to the front of fine filter 54. Cap 74 and its associated leakage paths 96 effectively constitute an inertial filter for separation of the gas to be measured from entrained water droplets and large particulates. Leakage paths 96 and sample channels 97 additionally constitutes of a coarse filter for additional removal of entrained water droplets and large particulates. Gas then passes through fine filter 54. Fine filter 54 may be constructed of quartz wool or the like. Next, the sample passes through channel 98 to capillary tube 56. Although not evident in FIG. 4, support tube 93, which is typically made of Teflon® material, surrounds tube 56 to provide mechanical support at this point. Similarly, support tube 94 supports cal gas capillary tube 76. Support tubes 93 and 94 are maintained in position by spacer 78. Though not shown, support tubes 93 and 94 extend the full length of body 72.

Heating means, such as heater wire 92, which is typically made of 316 stainless steel or suitable corrosion-resistant material, may be provided in the case in which the stack gases are fully saturated with water vapor or other condensible material. Wire 92 serves to heat the cavity of filter holder 55 in which fine filter 54 is located. Heater wire 92 further serves to warm sample gas capillary tube 56 and cal gas capillary tube 76 to prevent condensation in either region. Wire 92 then forms a coil 99 around the outside of filter holder 55 by entering through the annular space between tube 56 and support tube 93 and returns similarly through the space between cal gas tube 76 and its support tube 94. Filter holder 55 may be made of Teflon® material and is further equipped with O-rings, such as 95, which protect wire 92 and the general interior region of probe 72 from corrosive attack by acid gases and from condensation of stack moisture.

It can thus be seen that a novel system of extracting gas sampling for the analysis of process gases or fossil fuel combustive gases has been provided. The dew-point lowering required for sample transport without heated lines is accomplished by a combination of volumetric dilution and transport under substantial vacuum. Other benefits include reduced usage of dilution gas sufficient to permit use of bottled dilution gases, measurement of species that could not be measured were the volumetric dilution too high, fast response time, and flexibility in setting dilution ratios.

Referring now to the second embodiment shown in FIGS. 6 thru 9, we provide a housing 100 with cover 101 which contains a mixing conduit or dilution chamber 102. A probe housing 104 extends from the main housing 100. The device is fitted into an opening in a stack indicated by stack walls 103 shown in chain line. At the distal end of the probe assembly we provide a removable end housing 106. That housing 106 consists of a main body portion 107 from which an annular flange 108 extends. A sample gas channel 109 and calibration gas channel 116 are provided through the main body 107. The stack gas sample is collected and flows through channel 109 and conduit 114 to the mixing chamber. Sample conduit 114 is inserted into counterbore 170 in the end housing 106 Similarly, calibration gas conduit 116 is inserted into counterbore 171. A pair of ferrule-type bulk head valves 111 and quick release couplings 112 connect the end housing to sample conduit 114 and calibration gas conduit 116. Insulating sleeeves 117 are provided around the full length of sample conduit 114 and calibration gas 116. A heater wire 118 passes through the insulating sleeve 117 and surrounds the body 107 of the removable end housing 106. A heater conduit 119 permits the heater wire 118 to pass through the end housing 106 and then be coiled as coil section 118. The heat wire 118 maintains the sample at a high temperature, preferably about 250° F., until the sample reaches the dilution chamber 102 which is also heated. A course mesh filter 120 is positioned over a collection orifice 121. Preferably this filter is sized at from 0.05 to 0.15 mesh. Within collection orifice 121 we provide a glass wool filter 122 and a Teflon filter 124. The mesh filter 120 is preferably made of Teflon polymer or other hydrophobic material. Its function is to collect and coalese moisture in the sample passing through the filter which moisture would then drip from the mesh filter. Glass wool filter 122 and Teflon filter 124 prevent particulates from entering into the sample channel 109. The annular collar 108 surrounding the end of the probe keeps rain and other material which may be falling down the stack away from the collection orifice and filters 120 and 122. We prefer to provide O-ring seals 125 between the end housing 106 and probe housing 104.

The sample conduit 114 and cal gas conduit 116 are telescopically connected to the main housing at connections 126. Thus, it is a relatively simple matter to pull the end housing 106 from the probe housing 104 and disconnect the couplings 112 to remove end housing 106 from the system. Consequently, it is relatively easy to routinely clean or replace the filters used in this portion of the probe as well as the sample conduit 114 and cal gas conduit 116.

Figure 8:
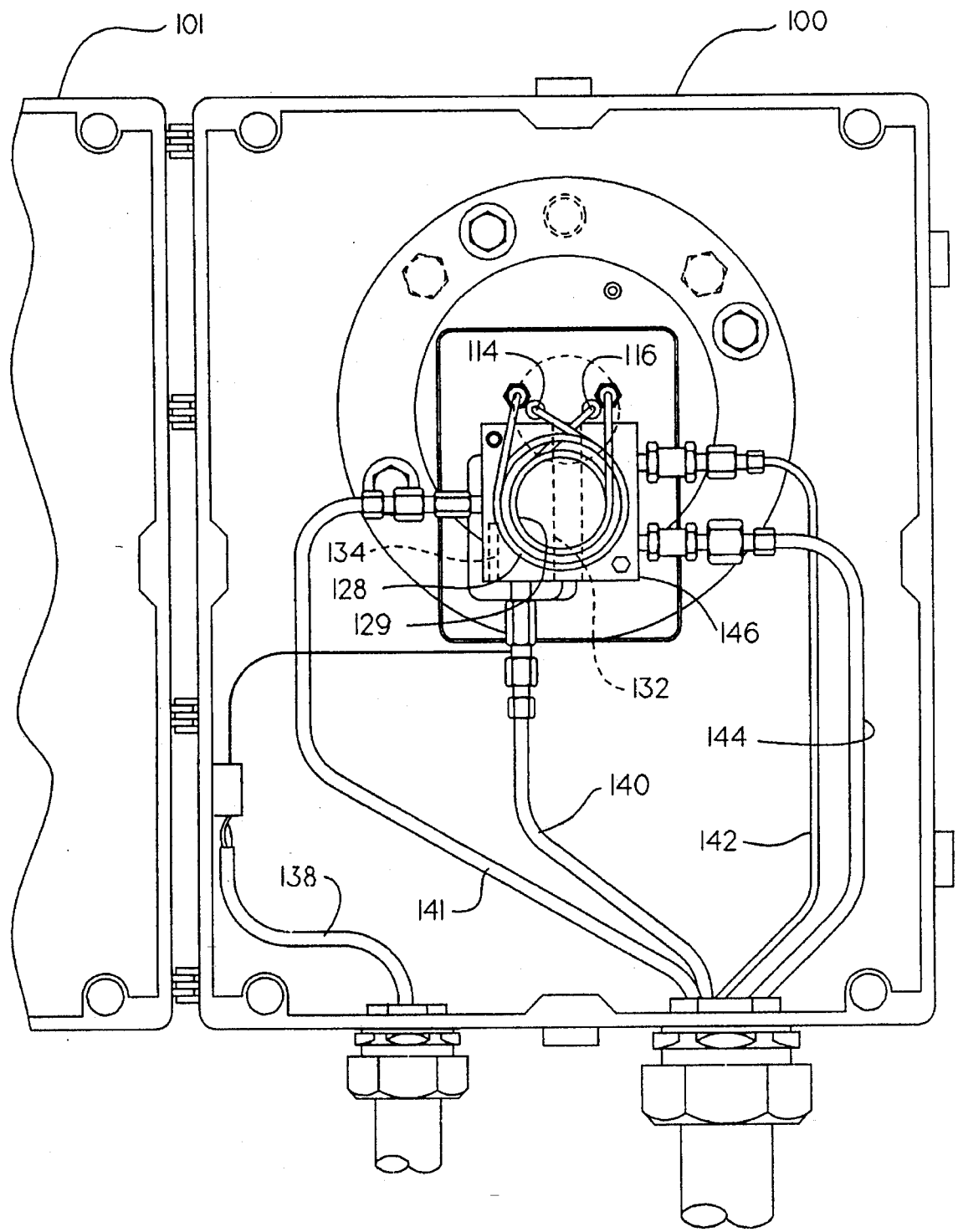
FIG. 8 is an end of the embodiment of FIG. 6 with the cover open.

Within housing 100 the sample conduit 114 continues to form a coil 128 which then is coupled to dilution chamber 102 within a housing 146. Cal gas conduit 116 continues to form coil 129. Coil 129 is within coil 128 and line 116 established line 114 in housing 110. Therefore, coil 129 and line 116 can only be seen in the housing from the view of FIG. 8. A cartridge heater 132, shown in chain line in FIG. 8, is provided in the housing 146 to maintain the dilution chamber 102 at an elevated temperature. Also, provided within the housing is a temperature probe or thermister 134 which monitors the temperature of the dilution chamber 102. Thus, the sample is maintained at an elevated temperature from the point of collection through dilution in the dilution chamber. A buss 136 is provided within the housing 100 to make electrical connections to cartridge heater 132 and thermister 134 as well as to the heater wire 118 which surrounds the sample conduit 114. Power is supplied to the buss 136 by cable 138 which also carries wires from the temperature gauge and heater controller which are normally located near the analyzer remote from the collection probe.

Figure 9:
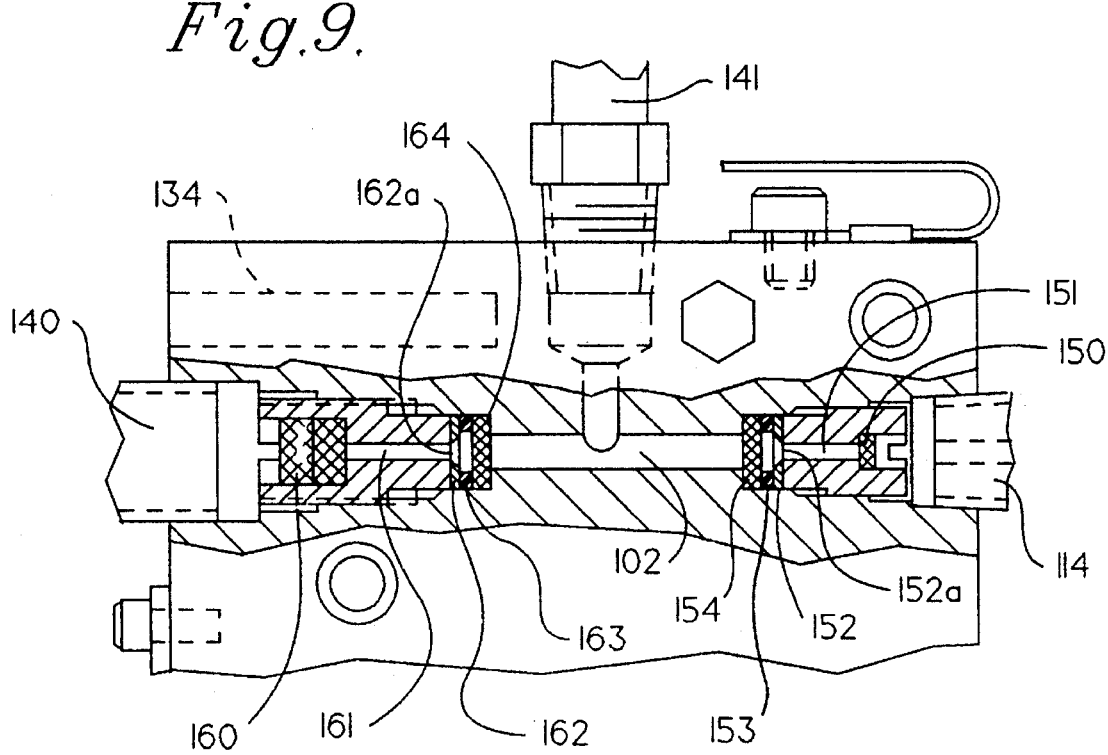
FIG. 9 is a plan view partially in section of the mixing chamber.

In FIG. 9 there is shown the interior of the dilution chamber 102. A gas sample enters the dilution chamber through conduit 114. As the gas approaches the conduit it first goes through a filter 150, passageway 151 and first critical flow orifice 152a in orifice plate 152. Then the sample passes through a second coarse filter 154. Calibration gas enters housing 146 through line 142. The diluted sample is removed from the dilution chamber through line 141. An O-ring seal 153 is placed between filters 152 and 154. These filters and orifice plates are preferably made of a corrosion resistant alloy, such as Hastelloy 276 alloy. From the opposite end of the dilution chamber dilution gas enters through conduit 140. The dilution gas passes through a filter and heat exchanger 160, passageway 161, second critical flow orifice 162a in orifice plate 162, coarse filter 164. An O-ring 163 is placed between the filter 164 and orifice plate 162. Filters 164 is preferably made of the same corrosion resistant alloy as filters 150 and 154. The larger filter 160 is made of a heat conductive material such as a copper alloy and functions to heat the dilution air as it enters the dilution chamber. The first and second critical flow orifices are sized to maintain a constant dilution ratio independent of minor fluctuations in the vacuum being drawn through conduit 141. We prefer to size the first critical flow orifice 152a at 0.0012 inches in diameter and the second critical flow orifice 162a at 0.006 inches in diameter.

It will be recalled that the entire housing 146 containing mixing chamber 102 has been heated by a cartridge heater 132 shown in chain line in FIG. 8. Within the dilution chamber 102 the dilution gas and sample gas mix to a desired ratio. Then the mixture is drawn through conduit 141 by a vacuum pump (not shown) connected to the sample line 141. We prefer that the dilution chamber be maintained at subatmospheric pressures preferably ranging from 0.5 to 0.15 atmospheres to ensure critical flow through the orifices 152a and 162a and also to ensure rapid transit of the sample from the mixing chamber to the anlayzer and to maintain a low dew point. As previously mentioned, within the dilution chamber we usually achieve dilution ratios ranging from 10:1 to 100:1 dilution gas to sample gas. The dilution chamber as well as the sample lines are made of non-corrosive materials which are suitable for withstanding the elevated temperatures encountered during operation. Preferably, these materials also will not be adversely affected by temperatures normally encountered in the environment should the probe not be in use and the heating elements not have been activated.

As certain presently preferred embodiments have been described and shown herein, it is to be understood that various other embodiments and modifications can be made within the scope of the following claims.

We claim:

1. An apparatus for collecting a sample stream from a system containing at least one gas comprising:

a) a collection probe adapted to draw a portion of at least one gas from the system;

b) a first conduit connected to the probe and having a first critical flow orifice therein through which the portion of at least one gas is drawn from the system;

c) means for supplying a dilution gas;

d) a second conduit connected to the means for supplying a dilution gas and having a second critical flow orifice through which the dilution gas is drawn;

e) a dilution chamber attached to the first and second conduits in which the portion drawn from the system and the dilution gas are mixed to form a mixture;

f) a third conduit connected to the dilution chamber through which a diluted sample is drawn; and g) at least one pump connected to the third conduit for drawing a vacuum on the connect mixture and repressurizing the mixture, the vacuum being sufficient to induce critical flow through the first critical flow orifice and the second critical flow orifice wherein the first and second critical flow orifices are sized to maintain a constant dilution ratio independent of minor fluctuations in the vacuum being drawn.

2. The apparatus of claim 1 also comprising a filter attached to the collection probe.

3. The apparatus of claim 1 wherein the dilution gas is at least one compressed gas cylinder.

4. The apparatus of claim 1 also comprising means for supplying at least one calibration gas connected to the collection probe.

5. The apparatus of claim 1 also comprising means for mounting the collection probe in a stack.

6. The apparatus of claim 1 also comprising at least one analyzer connected to the third conduit.

7. The apparatus of claim 1 wherein the vacuum creates a pressure in the mixture not greater than 0.40 atmospheres.

8. The apparatus of claim 1 wherein the first critical flow orifice is 0.0009 inches and the second critical flow orifice is 0.0045 inches.

9. The apparatus of claim 1 wherein the first and second critical flow orifices and the dilution chamber are made of corrosion resistant material selected from the group consisting of corrosion resistant metal alloys, glass, and corrosion resistant polymeric materials.

10. The apparatus of claim 1 also comprising at least one heating means attached to at least one of the first conduit, the second conduit and the dilution chamber.

11. The apparatus of claim 1 also comprising at least one analyzer connected to the third conduit.

* * * * *